US011382693B2

(12) United States Patent
Harrah et al.

(10) Patent No.: US 11,382,693 B2
(45) Date of Patent: Jul. 12, 2022

(54) MEDICAL DEVICE AND METHODS OF USE

(71) Applicant: Boston Scientific Scimed, Inc., Maple Grove, MN (US)

(72) Inventors: Timothy P. Harrah, Cambridge, MA (US); Christopher L. Oskin, Grafton, MA (US); Derrick Lenz, Pompton Plains, NJ (US); Arpita Banerjee, Bangalore (IN); Sandesh Gavade, Bangalore (IN); Abhijit Takale, Pune (IN); Pavan Misra, Bangalore (IN); Michael S.H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 670 days.

(21) Appl. No.: 15/421,044

(22) Filed: Jan. 31, 2017

(65) Prior Publication Data
US 2017/0215965 A1 Aug. 3, 2017

Related U.S. Application Data

(60) Provisional application No. 62/290,219, filed on Feb. 2, 2016.

(51) Int. Cl.
*A61B 18/26* (2006.01)
*A61M 25/00* (2006.01)
(Continued)

(52) U.S. Cl.
CPC .......... *A61B 18/26* (2013.01); *A61B 1/00094* (2013.01); *A61B 1/00137* (2013.01);
(Continued)

(58) Field of Classification Search
CPC . A61B 1/00101; A61B 1/00135; A61B 1/015; A61B 1/12; A61B 2217/007; A61B 1/00094
(Continued)

(56) References Cited

U.S. PATENT DOCUMENTS 5,536,234 A * 7/1996 Newman ............ A61B 1/00091
600/104
6,547,724 B1 * 4/2003 Soble .................... A61B 1/005
600/156
(Continued)

FOREIGN PATENT DOCUMENTS

CN 1290150 A 4/2001
WO WO 00/04838 A1 2/2000
WO 2013090827 A1 6/2013

OTHER PUBLICATIONS

International Search Report and Written Opinion for International Application No. PCT/US2017/015847, dated May 17, 2017 (9 pages).

*Primary Examiner* — Alexandra L Newton
(74) *Attorney, Agent, or Firm* — Bookoff McAndrews, PLLC

(57) ABSTRACT

The present disclosure is directed to a medical device. Systems and methods are provided for utilizing a laser to break a kidney stones into smaller fragments and/or dust, and removing particles, stone fragments and/or stone dust from a patient. The medical device may include a tube having a distal end and a proximal end, a first lumen extending from the proximal end to the distal end of the tube and in fluid communication with the distal end and a plurality of side ports located at a distal portion of the tube, and a second lumen extending from the proximal end to the distal end of the tube.

20 Claims, 8 Drawing Sheets

(51) Int. Cl.
  *A61B 1/00* (2006.01)
  *A61B 1/018* (2006.01)
  *A61B 1/015* (2006.01)
  *A61B 1/06* (2006.01)
  *A61B 1/12* (2006.01)
  *A61B 18/22* (2006.01)
  *A61B 18/00* (2006.01)
  *A61B 18/24* (2006.01)

(52) U.S. Cl.
  CPC .............. *A61B 1/015* (2013.01); *A61B 1/018* (2013.01); *A61B 1/0684* (2013.01); *A61B 1/126* (2013.01); *A61M 25/003* (2013.01); *A61M 25/007* (2013.01); *A61B 18/245* (2013.01); *A61B 2018/00035* (2013.01); *A61B 2018/00511* (2013.01); *A61B 2018/00517* (2013.01); *A61B 2018/00625* (2013.01); *A61B 2018/00982* (2013.01); *A61B 2018/2266* (2013.01); *A61B 2218/002* (2013.01); *A61B 2218/007* (2013.01); *A61M 2025/004* (2013.01)

(58) Field of Classification Search
  USPC .......................................... 600/123, 153, 156
  See application file for complete search history.

(56) References Cited

U.S. PATENT DOCUMENTS

| | | | |
|---|---|---|---|
| 2002/0161358 A1 | 10/2002 | Liu et al. | |
| 2005/0171470 A1* | 8/2005 | Kucklick | A61M 1/0084 604/96.01 |
| 2009/0012362 A1* | 1/2009 | Kucklick | A61B 1/317 600/121 |
| 2011/0224489 A1 | 9/2011 | Deal et al. | |
| 2012/0277533 A1* | 11/2012 | Kucklick | A61B 1/00135 600/123 |
| 2013/0165944 A1* | 6/2013 | Gal | A61B 17/22 606/127 |
| 2013/0225937 A1* | 8/2013 | Schaeffer | A61M 3/0279 600/249 |
| 2014/0213850 A1* | 7/2014 | Levy | A61B 1/0615 600/156 |
| 2014/0275762 A1* | 9/2014 | Irby, III | A61B 18/26 600/103 |
| 2014/0276369 A1 | 9/2014 | Banko | |
| 2016/0106580 A1* | 4/2016 | Banko | A61F 9/00736 604/22 |
| 2016/0166320 A1 | 6/2016 | Ciulla et al. | |

* cited by examiner

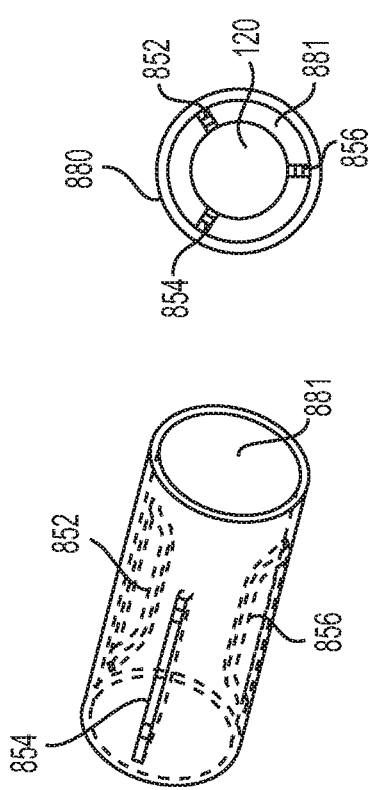
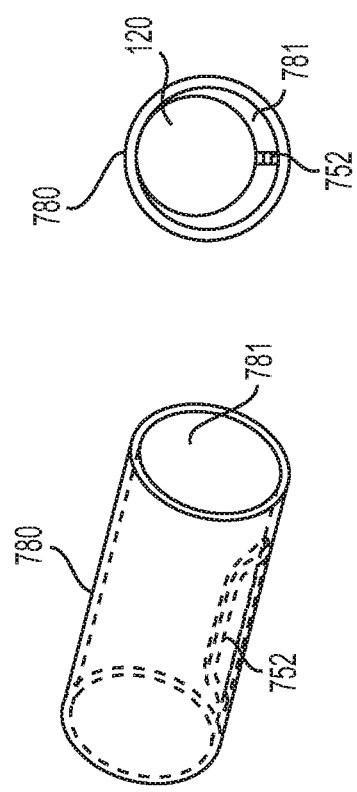
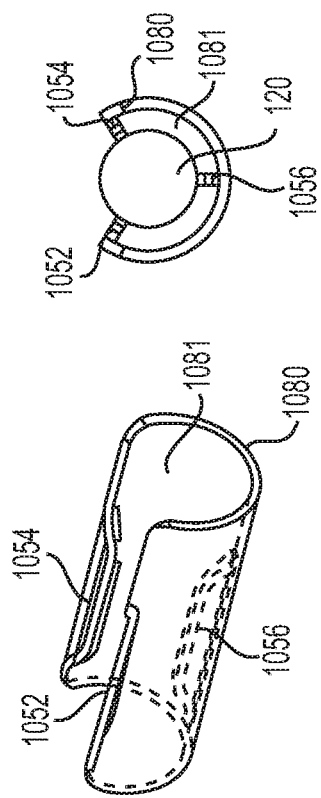
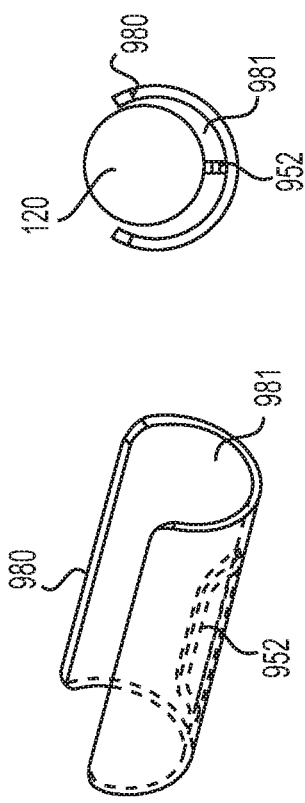

MEDICAL DEVICE AND METHODS OF USE

CROSS-REFERENCE TO RELATED APPLICATIONS

This application claims the benefit of priority of U.S. Provisional Application No. 62/290,219, filed Feb. 2, 2016, the entirety of which is incorporated by reference into this application.

TECHNICAL FIELD

The present disclosure relates generally to medical devices. More particularly, the disclosure relates to medical devices used, for example, in breaking objects into smaller particles, and removing the resulting particles from a patient. The disclosure also relates to methods of using such devices.

BACKGROUND OF THE DISCLOSURE

The incidence of hospitalization for the removal of urinary calculi, commonly referred to as kidney stones, has been estimated at 200,000 cases per year. A vast majority of these patients pass their stones spontaneously; however, in the remainder, the kidney stone(s) become impacted in the ureter, a muscle tube joining the kidney to the bladder. An impacted kidney stone is a source of intense pain and bleeding, a source of infection and, if a stone completely blocks the flow of urine for any extended length of time, can cause the loss of a kidney.

Various methods have been utilized to break the stone into smaller fragments. One such method is stone dusting. Stone dusting is used by some urologists to fragment and evacuate stones from a kidney and is often performed by a ureteroscope. Intense light energy from a laser within the ureteroscope breaks the stone into increasingly smaller pieces. Rather than breaking up the stone into chunks, which are removed by baskets, dusting generates very small fragments that are capable of being passed naturally. However, in some cases, these small stone fragments may not pass naturally. In theory, any of these small stone fragments that do not evacuate through natural urine flow, could be a seed for new stone growth. Thus, the application of suction may be employed to remove the stone dust. A pressure equilibrium should be maintained within the kidney and in order to apply suction, fluid should also be introduced. The disclosure addresses the above-mentioned process and other problems in the art.

SUMMARY OF THE DISCLOSURE

Aspects of the present disclosure provide devices and methods for breaking an object into smaller particles and removing said particles from portions of the human body.

It is to be understood that both the foregoing general description and the following detailed description are exemplary and explanatory only and are not restrictive.

In one example, a medical device may include a tube having a distal end and a proximal end, a first lumen extending from the proximal end to the distal end of the tube and in fluid communication with the distal end and a plurality of side ports located at a distal portion of the tube, and a second lumen extending from the proximal end to the distal end of the tube.

Examples of the medical device may additionally and/or alternatively include one or more other features. Features of the various examples described in the following may be combined unless explicitly stated to the contrary. For example, the tube may be in fluid communication with a cap located at the distal portion, and the cap may be removably attached to the tube. The medical device may include a laser fiber disposed within the first lumen. The plurality of side ports may be disposed on a circumference of the distal portion. The plurality of ports may be disposed on less than 270 degrees of the circumference of the distal portion. The medical device may include a vacuum source connected to the second lumen and a fluid supply assembly connected to the first lumen. The medical device may include an illumination device and an imaging device. The plurality of side ports may include a plurality of linear rows. The plurality of side ports may include at least three ports. The medical device may include a laser fiber holder. The laser fiber holder may be at least partially disposed the first lumen.

In another example, a method operating a medical device may include positioning a distal end of a medical device at a target area, the medical device including a first lumen and a second lumen, wherein the first lumen is in fluid communication with a distal end of the medical device and with side ports on a distal portion of the medical device, supplying fluid through the first lumen, and applying suction through the second lumen.

Examples of the method of operating the medical device may additionally and/or alternatively include one or more other features. For example, a laser fiber holder may be at least partially disposed within the first lumen. The method may include inserting a laser fiber in the first lumen and extending the laser fiber to the distal end of the medical device, and initiating the laser.

In one example, a laser fiber holder may include a first proximal hole and a second distal hole opposite the first, configured to stabilize a laser fiber extending through the first hole and the second hole.

Examples of the laser fiber holder may additionally and/or alternatively include one or more other features. Features of the various examples described in the following may be combined unless explicitly stated to the contrary. For example, the laser fiber holder may be sized to be secured within a lumen. The laser fiber holder may have an inverted configuration and an extended configuration. The laser fiber holder may include at least one ramp. The laser fiber holder may include at least one helix. The laser fiber holder may be configured to allow fluid to flow through the laser fiber holder.

BRIEF DESCRIPTION OF THE DRAWINGS

The accompanying drawings, which are incorporated in and constitute a part of this specification, illustrate various examples and together with the description, serve to explain the principles of the disclosure.

FIGS. 7A and 7B illustrate an exemplary perspective view and exemplary cross-section of an alternative exemplary laser fiber holder;

FIGS. 8A and 8B illustrate an exemplary perspective view and exemplary cross-section of an alternative exemplary laser fiber holder;

FIGS. 9A and 9B illustrate an exemplary perspective view and exemplary cross-section of an alternative exemplary laser fiber holder;

FIGS. 10A and 10B illustrate an exemplary perspective view and exemplary cross-section of an alternative exemplary laser fiber holder;

DETAILED DESCRIPTION

Figure 1:
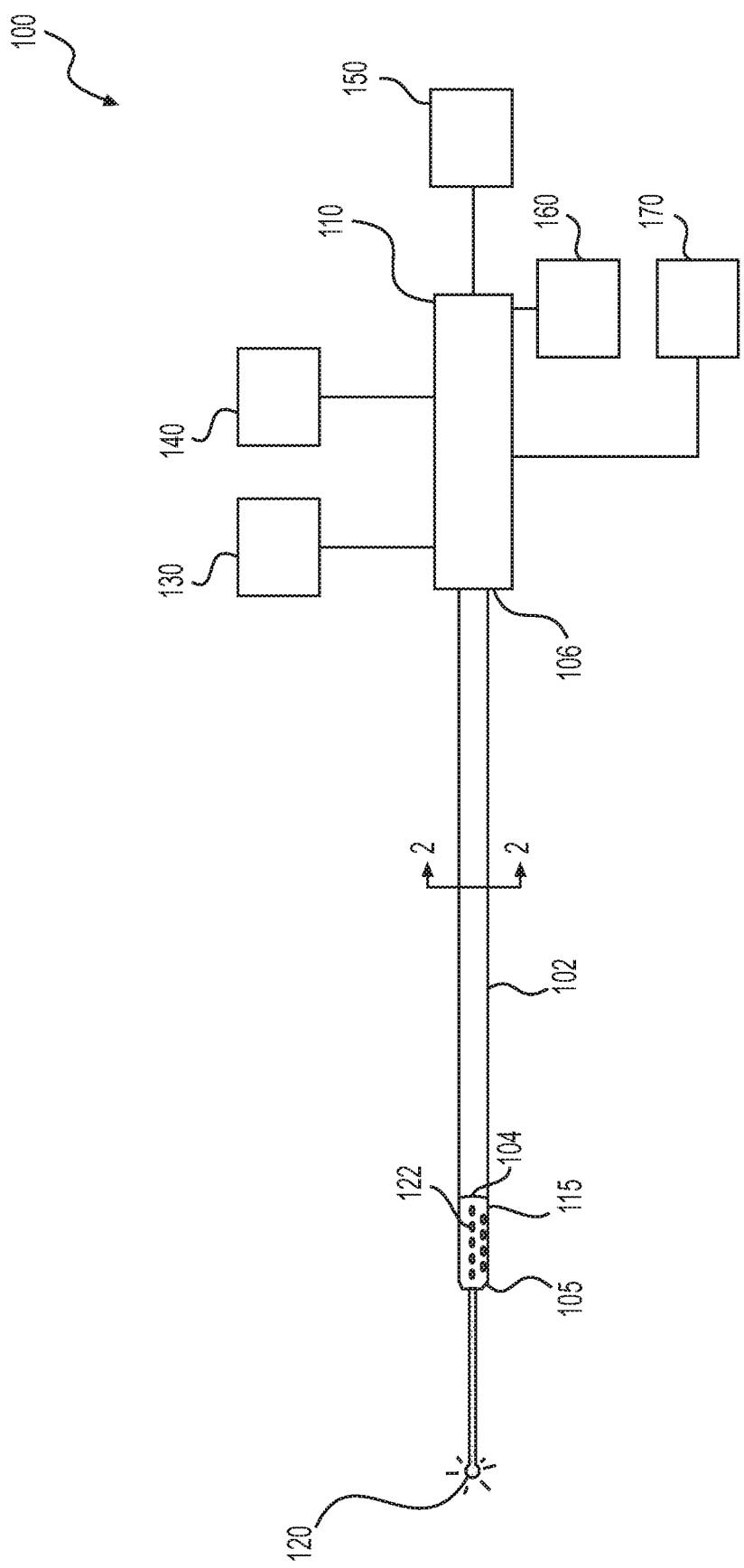
FIG. 1 illustrates an exemplary medical device, including a tube, a distal portion, a handle portion, a fluid supply assembly, a laser source, an illumination source, an imaging apparatus, and a vacuum source.

Reference is now made in detail to examples of the present disclosure, examples of which are illustrated in the accompanying drawings. Wherever possible, the same reference numbers will be used throughout the drawings to refer to the same or like parts. The term "distal" refers to a position farther away from a user end of the device. The term "proximal" refers a position closer to the user end of the device. As used herein, the terms "approximately" and "substantially" indicate a range of values within +/−5% of a stated value.

Overview

Aspects of the present disclosure relate to systems and methods for breaking kidney stones into smaller particles and removing those particles from the body. The medical devices described herein may work by positioning within a body, a ureteroscope and a laser disposed within a lumen of the ureteroscope. The laser may be used to break up kidney stones into particles. During the laser process or after removal of the laser from the body and/or lumen, the ureteroscope may vacuum the resulting particles from the body. More specifically, in some examples, the ureteroscope includes a tube with at least two lumens. A first lumen may be a working channel configured to receive and position a laser and provide fluid to irrigate a target area. A second lumen may provide suction to carry out the irrigation fluid along with the particles. In some examples, the tube may connect to a distal portion or a cap. The first lumen of the tube may connect to a corresponding first lumen in the cap. The first lumen of the cap may connect to both a substantially distal-facing opening at a distal end of the cap, as well as, a plurality of ports around the circumference of the cap. In some examples, the medical device may not include a cap and the tube will be designed with a distal-facing opening and a plurality of ports around a circumference of the tube in fluid communication with the first lumen.

The target area may be any location. In some examples, the target area may be anywhere within a urinary tract including, but not limited to, a kidney. In some examples, the target area may be a site in the body where a kidney stone(s) is known or suspected to be located.

Aspects of the present disclosure may additionally or alternatively relate to systems and methods for securing a laser fiber within a lumen of a medical device. For example, a laser fiber may be secured within a working channel of a ureteroscope to ensure that flow within the body, including introduced irrigation fluid, kidney stones and particles, and/or the application of suction do not unintentionally move the laser fiber. Such a laser fiber holder may also ensure that as the distal end of the ureteroscope moves (including any associated imaging devices), the laser fiber matches these movements. The laser fiber holders described herein are not limited to the medical devices and lumens described herein, but may be used with any medical device and/or any lumen to secure, stabilize, and/or control the movements of a laser fiber.

Detailed Examples

Figure 2:
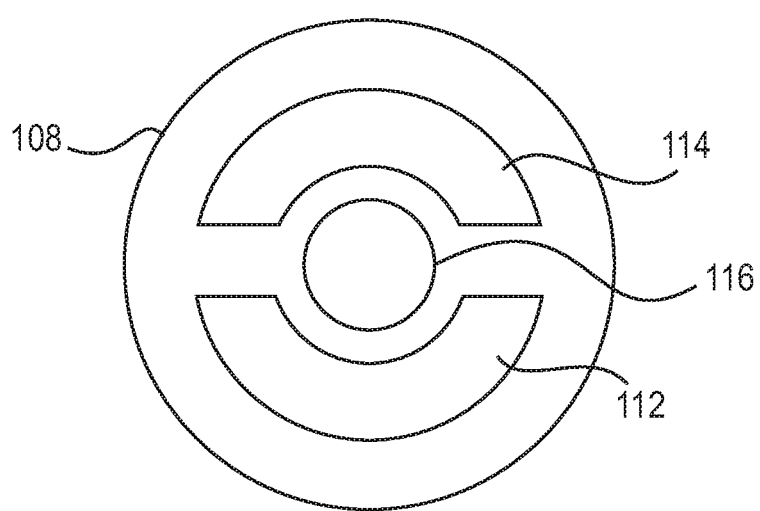
FIG. 2 illustrates an exemplary cross-section of the tube taken at 2-2 of FIG. 1.

FIG. 1 illustrates an exemplary medical device 100 for breaking an object into fragments and removing the resulting fragments from the target area, e.g., the kidney. The device 100 may include a tube 102 and/or a distal portion 115. Tube 102 may be a hollow, flexible, elongate tube having a proximal end 106 and a distal end 104. Distal end 104 of tube 102 may either include an integral distal portion 115 or distal end 104 of tube 102 may be coupled to a separate and distinct distal portion 115. Distal portion 115 and/or tube 102 may further include independent first and second lumens 112 and 114 (FIG. 2). Proximal end 106 of tube 102 may be coupled to a handle portion 110. The handle portion 110 and/or the proximal end 106 of tube 102 may be attached to a laser control 130, a fluid supply assembly 140, a vacuum source 150, an illumination source 160, and/or an imaging apparatus 170.

A. The Tube

Figure 4:
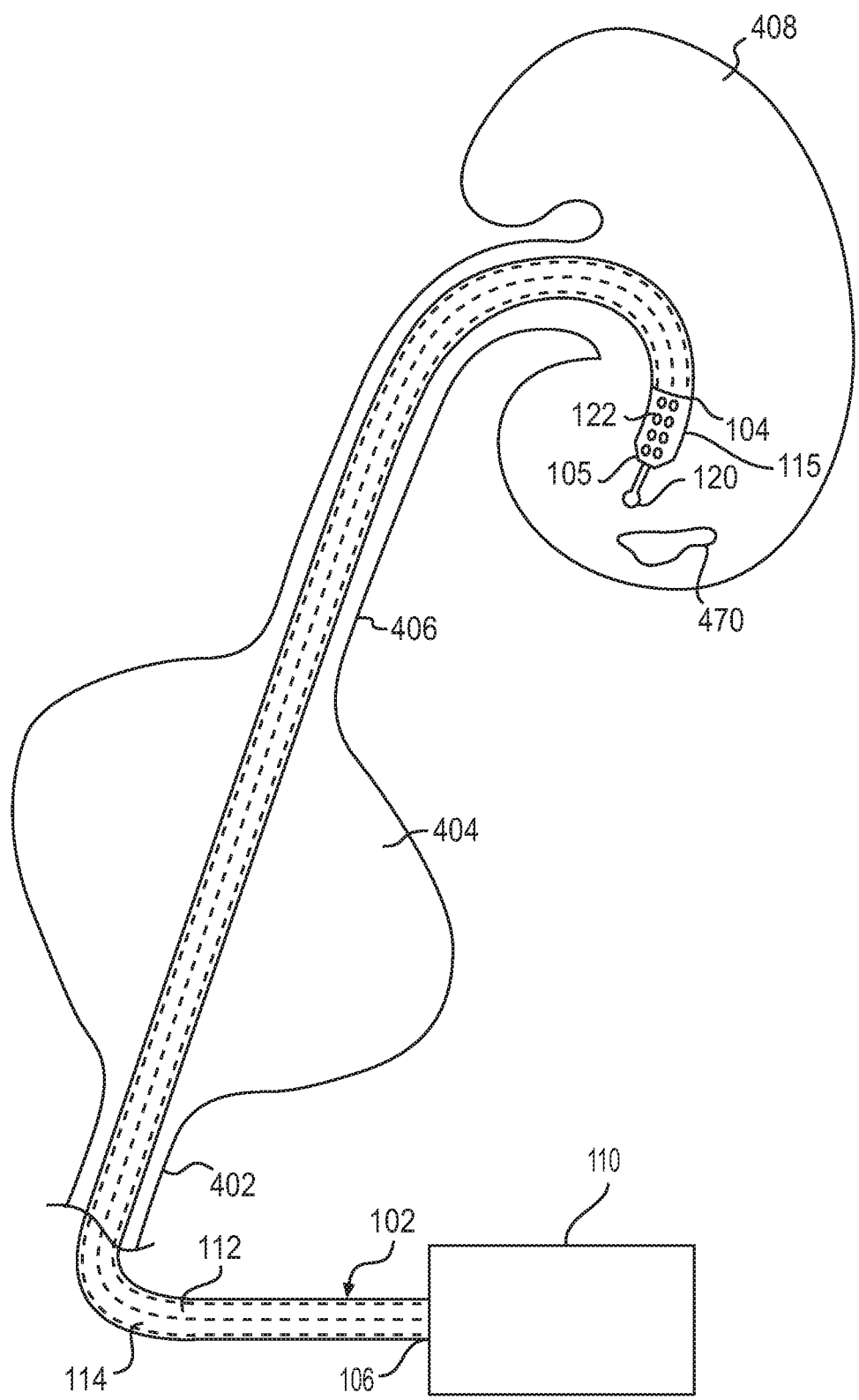
FIG. 4 illustrates an exemplary medical device extending into a patient's body.

As noted above, tube 102 may include two independent lumens, first lumen 112 and second lumen 114. While two lumens are illustrated in FIG. 4, tube 102 may include any number of lumens. For example, as shown in FIG. 2, tube 102 may include three lumens; a first lumen 112 for introduction of fluid and a laser fiber, a second lumen 114 for the application of suction, and a third lumen 116 for wires/fibers/etc. necessary for controlling and communication with an imaging and/or illumination device(s) located at a distal end of the medical device 100. In some examples, a fourth and/or fifth lumen may be included for, e.g., a separate lumen exclusively for the introduction of the laser fiber or an additional lumen for the introduction of fluid through the side ports. The lumens included in tube 102 may be any size, shape, and/or in any configuration. An exemplary cross-section of tube 102, including first lumen 112, second lumen 114, and third lumen 116 will be described in further detail below with respect to FIG. 2.

Tube 102 and/or distal portion 115 may be circular, ovoidal, irregular, and/or any shape suitable to enter a body. Further, tube 102 may have the same shape or a different shape than distal portion 115. For example, both tube 102 and distal portion 115 may be substantially circular. Tube 102 may have a uniform shape from proximal end 106 to distal end 104 and/or from proximal end 106 to distal end 105 of distal portion 115. In some examples, tube 102 (and/or distal portion 115) may have a varying shape, such as a taper at the distal end to facilitate insertion within the body.

Depending upon the particular implementation and intended use, the length of tube 102 may vary. Similarly, depending upon the particular implementation and intended use, tube 102 can be rigid along its entire length, flexible along a portion of its length, or configured for flexure at only certain specified locations. In one example, tube 102 may be flexible, adapted for flexible steering within bodily lumens, as understood in the art. For example, tube 102 can include a steering system (not shown) to move at least a portion (e.g., distal end 104) up/down and/or side-to-side. Additional degrees of freedom, provided for example via rotation, translational movement of tube 102, or additional articulation of bending sections, may also be implemented. Examples of such steering systems may include at least one of pulleys, control wires, gearing, or electrical actuators.

Tube 102 and/or distal portion 115 may be formed of any suitable material having sufficient flexibility to traverse body cavities and tracts. In general, tube 102 and/or distal portion 115 may be made of any suitable material that is compatible with living tissue or a living system. That is, the tube 102 and/or distal portion 115 may be non-toxic or non-injurious, and it should not cause immunological reaction or rejection. In some examples, tube 102 and/or distal portion 115 may be made of polymetric elastomers, rubber tubing, and/or medically approved polyvinylchloride tubing. Polymeric elastomers may be, for example, EVA (Ethylene vinyl acetate), silicone, polyurethane, and/or C-Flex. Tube 102 and/or distal portion 115 may be made of the same or different material.

FIG. 2 illustrates a cross-sectional view of tube 102 depicting first lumen 112, second lumen 114, and third lumen 116. This view may, for example, be at line 2-2 of FIG. 1, proximal end 106 of tube 102, distal end 104 of tube 102, and/or at the proximal end of distal portion 115 (as described in more detail below). As shown, first lumen 112 and second lumen 114 may be an arc- or curved-shaped lumen and third lumen 116 may be substantially circular in shape and disposed within a wall within tube 102 between first lumen 112 and second lumen 114. The size and shape of first lumen 112, second lumen 114, and/or third lumen 116 are not limited thereto. For example, first lumen 112 and second lumen 114 may be substantially semi-circular in shape and either the wall between the two may be larger to accommodate third lumen 116 without effecting the shape of lumens 112 and 114 or third lumen 116 may have a smaller cross-sectional area than shown in FIG. 2. In some examples, lumens 112 and 114 have approximately the same cross-sectional shape and size. In some examples lumen 112 and 114 have a different shape and/or size. Any of lumens 112, 114, and/or 116 may be configured to supply fluid, apply suction, and/or transport visualization devices or laser fibers. Lumen 116 may have a diameter of approximately 2×0.5 mm to approximately 3.5×1.5 mm, approximately 2.4×0.8 mm to approximately 3.2×1.6 mm, or approximately 2.6×1 mm to approximately 3×1.4 mm. Lumen 114 and 112 may have a surface area of approximately 1.2-2.2 mm$^2$, approximately 1.4-2 mm$^2$, or approximately 1.6-1.8 mm$^2$. In some examples, lumen 114 and 112 are chamfered surfaces.

First lumen 112, second lumen 114, and/or third lumen 116 may include any suitable coating. For example, first lumen 112, second lumen 114, and/or third lumen 116 may include a layer of lubricous material, for example, to facilitate insertion of any instrument and/or device (e.g., laser fiber 120 through first lumen 112) or prevent clogging (e.g., as a result of stone fragments/dust in second lumen 114). First lumen 112, second lumen 114, and/or third lumen 116 may be defined by elongate hollow lumens that extend within tube 102.

Figure 3A:
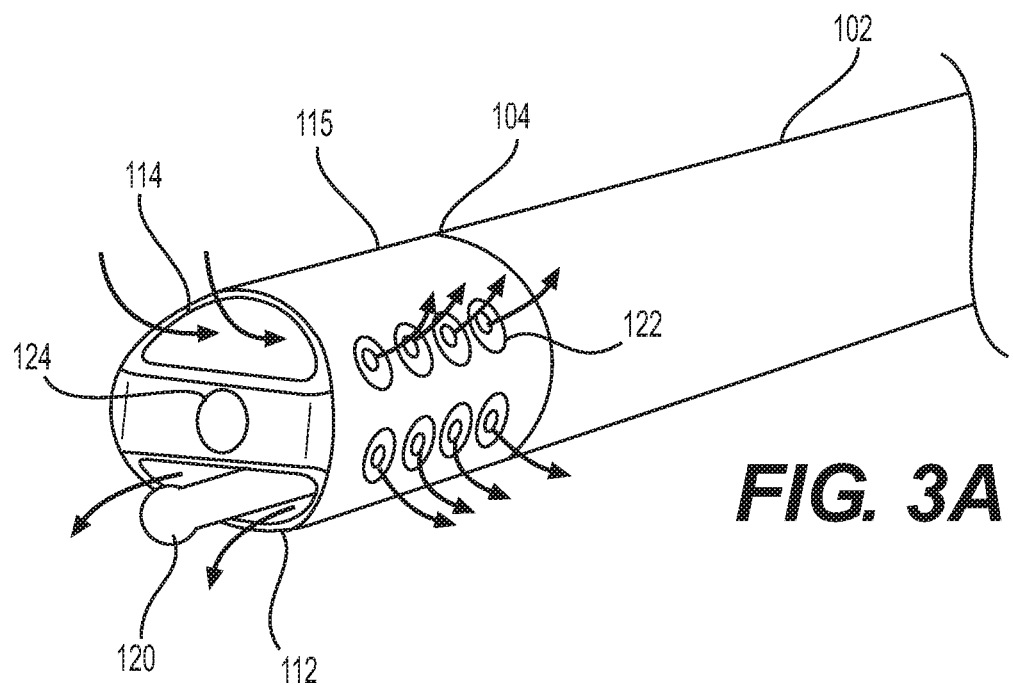
FIGS. 3A and 3B illustrate an exemplary perspective view and an exemplary side view of a distal end of the medical device of FIG. 1.
Figure 3B:
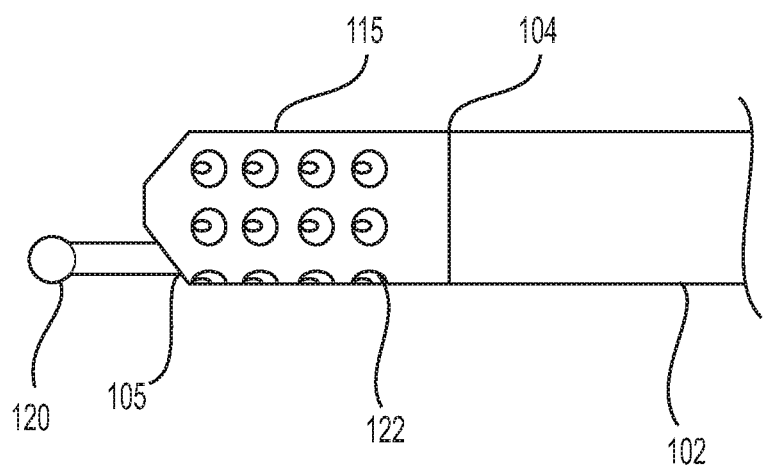
Figure 5A:
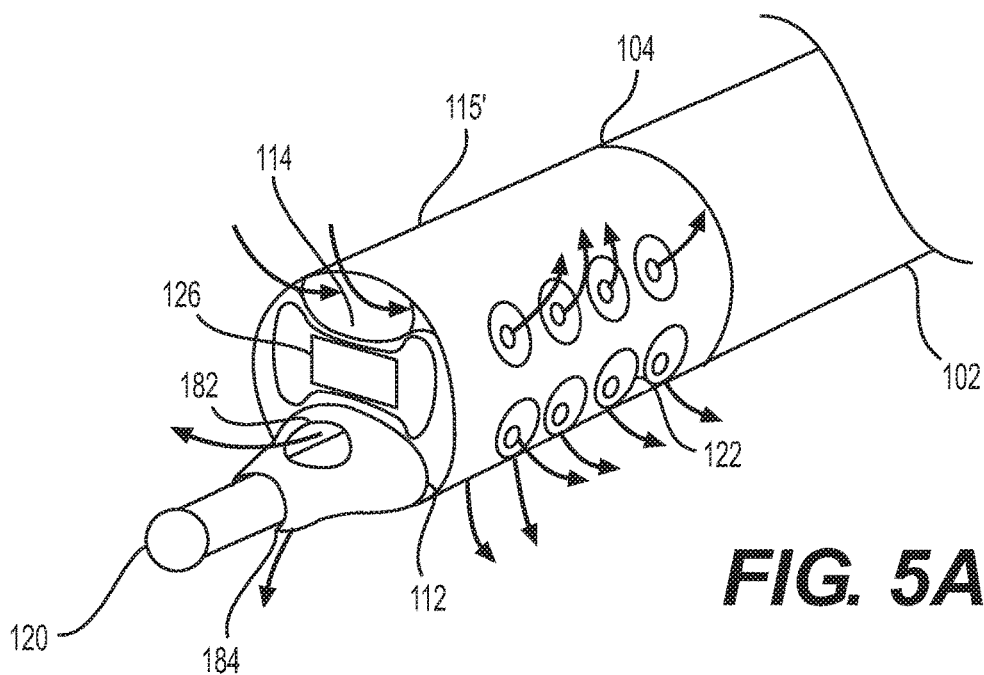
FIGS. 5A and 5B illustrate an exemplary perspective view and an exemplary side view of an alternative distal end of the medical device of FIG. 1.
Figure 5B:
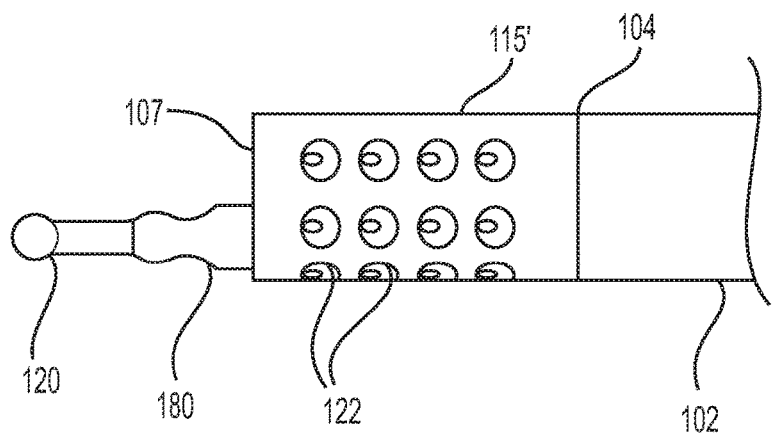

First lumen 112, second lumen 114, and/or third lumen 116 may extend between proximal end 106 and distal 104. First lumen 112 may be open (e.g., open to a body cavity like a kidney) at the distal end 104 of tube 102 to allow introduction of a laser fiber 120 and/or flow of irrigation fluid. In examples in which a cap (e.g., distal portion 115) is attached to distal end 104 of tube 102, first lumen 112 may align with an opening within distal portion 115 to extend the first lumen 112 through to the distal end 105 of the distal portion 115 and/or side ports 122 to allow the flow of irrigation fluid within first lumen 112 to exit into the kidney at a plurality of locations along an exterior circumference of distal portion 115. The distal opening of first lumen 112 (e.g., at distal end 105 of distal portion 115) may be substantially perpendicular to the tube (e.g., as shown in FIGS. 5A and 5B), may be tapered or angled (e.g., as shown in FIGS. 3A and 3B), or may be in any other suitable shape, size, and/or orientation. Within distal portion 115 (e.g., between distal end 105 of distal portion 115 and distal end 104 of tube 102), first lumen 112 may fork and/or include a plurality of small branches at multiple locations to place first lumen 112 in fluid communication with a plurality of ports 122. The proximal end of first lumen 112 may have any shape or configuration. For example, first lumen 112 may have two openings or may fork at or near the proximal end 106 of tube 102. First lumen 112 may be configured in any way that would allow for first lumen 112 to be simultaneously connected to fluid supply apparatus 140 and laser control 130. This may allow laser fiber 120 to be disposed within first lumen 112 at the same time fluid is introduced through first lumen 112 to side ports 122 and/or distal end 105.

Second lumen 114 may be open (e.g., open to a body cavity like a kidney) at the distal end 105 of distal portion 115 of tube 102 to provide for the application of suction. In examples in which a cap (e.g., distal portion 115) is attached to distal end 104 of tube 102, second lumen 114 may align with an opening within distal portion 115 to extend the second lumen 114 through to the distal end 105 of the distal portion 115. The distal opening of second lumen 114 (e.g., at distal end 105 of distal portion 115) may be substantially perpendicular to the tube (e.g., as shown in FIGS. 5A and 5B), may be tapered or angled (e.g., as shown in FIGS. 3A and 3B), or may be in any other suitable shape, size, and/or orientation. Second lumen 114 may be in fluid communication with vacuum source 150.

As shown in FIGS. 3A and 3B, distal portion 115 may include a plurality of side ports 122. In some examples, ports 122 may be substantially or at least partially facing radially outward (e.g., approximately perpendicular to the longitudinal axis of tube 102) or ports 122 may be angled toward distal end 105 of distal portion 115 so that the irrigation fluid is introduced toward the distal end of the medical device. The angling of fluid introduced through ports 122 may also include angling the passage(s) (e.g., branches extending from first lumen 112) connected to ports 122. The angle of the introduction of fluid may be greater than approximately 10 degrees from longitudinal axis of first lumen 112 to less than approximately 90 degrees from the longitudinal axis of first lumen 112, preferably between approximately 20 degrees and approximately 80 degrees. In some examples, the preferred angle of introduction of fluid may be between approximately 30 degrees and approximately 60 degrees. Angling the introduction of fluid toward the distal end 105 of distal portion 115 may assist in pushing stone fragments/dust toward the vacuum, e.g., distal opening of second lumen 114.

There may be any number of side ports 122, spaced any distance apart, and located anywhere along the radial surface of distal portion 115. In some examples, distal portion 115 includes at least three side ports. The plurality of ports may include any numbers of rows. In the examples illustrated herein, the rows are substantially linear, but the plurality of ports is not limited thereto and may be in any pattern. In some examples, each row includes at least three ports. In the example shown in FIG. 3A, each row includes four ports. In the example illustrated in FIG. 1, a first row includes five ports and a second row includes four ports. Each row, however, may include any number of ports. The ports may be disposed on any portion of the circumference. For example, the ports may be located on an entire 360 degrees of the circumference of distal portion 115. In other examples, like those illustrated in FIGS. 3A and 5A, ports 122 may be disposed on less than between approximately 300 degrees and approximately 200 degrees and greater than approximately 45 degrees or approximately 90 degrees, or disposed on approximately 180 degrees of the circumference of distal portion 115. Ports 122 may only be on a portion (e.g., less than 360 degrees) of the outer surface, so that ports 122 are adjacent to first lumen 112 (e.g., the lumen in fluid communication with fluid supply assembly 140). Otherwise, in examples in which ports 122 are disposed on 360 degrees of the outer surface, additional space may be required within tube 102 and/or distal portion 115 to provide access to first lumen 112 to ports that are adjacent to second lumen 114. For example, connecting lumens (e.g., to connect additional ports to fluid supply assembly 140) may be disposed radially outwardly of second lumen 114 and thus increase the outer diameter of distal portion 115 and/or decrease the internal diameter of lumens within distal portion 115. By positioning side ports 122 on the sides of tube 102, more surface area will be available on the distal face of tube 102 (e.g., by minimizing the volume of fluid through the distal end of first lumen 112 and thus cross-sectional area of first lumen 112 at the distal end). Thus, the cross-sectional area of distal opening of second lumen 114 may be maximized while providing sufficient inlet flow of irrigation fluid to provide a clear view for any imaging devices.

The side ports 122 may be any size and/or shape. For example, ports 122 may be substantially circular and may have a diameter of approximately 0.2 mm to approximately 0.8 mm, approximately 0.3 mm to approximately 0.6 mm, or approximately 0.3 mm to approximately 0.5 mm. In some examples, each of the plurality of ports 122 may have substantially the same diameter. In some examples, the diameter of each of port 122 may vary. In some examples, ports 122 may be located within substantially circular recesses. These recesses may prevent abrasion of a patient's tissue during insertion or removal of medical device 100 to and from the patient's body. The diameter of these recesses may be approximately 1.5 to approximately 3 times the diameter of its corresponding port 122, or approximately 2 times the diameter of its corresponding port. Ports 122 may be in any pattern. As shown in FIG. 3A, ports 122 may be in uniform rows. In some examples, the density of ports 122 may vary, e.g., ports may be closer together at the distal end than the proximal or vice versa. In some examples, the ports may be concentrated on the surface opposite the lumen used for suction (e.g., second lumen 114) or vice versa.

Distal end 105 of distal portion 115 of tube 102 may include visualization devices such as imaging and/or illumination device 124. These device(s) may be connected to imaging apparatus 170 and illumination source 160, respectively. As shown below in FIG. 3A, imaging and/or illumination device 124 may be disposed on a distal facing surface of distal portion 115. These devices and/or connecting wires may extend within the tube 102 (e.g., third lumen 116 of FIG. 2). For example, an imaging device may be a digital camera and signal and/or power lines may extend through third lumen 116. The illumination device may be an LED and a fiber may extend through lumen 116. Imaging and/or illumination device 124 may attach to the distal end 105 using known coupling mechanisms. Imaging and/or illumination device 124 may be any imaging device and/or illumination device known in the art. As shown in FIG. 3A, the imaging device and illumination device may have a substantially circular cross-section and/or may be integrated into a single unit. Additionally or alternatively, the visualization devices may be detachably introduced into tube 102 through other lumens, including first lumen 112 and/or second lumen 114 when required. For example, the proximal end of first lumen 112 and/or second lumen 114 may be forked to allow introduction of additional devices as well as a connection to either fluid supply apparatus 140 and/or vacuum source 150. Additionally or alternatively, first lumen 112 and/or second lumen 114 may include side port(s) at or near proximal end 106 for introduction of additional devices.

As mentioned above, distal end 104 of tube 102 may be permanently or removably coupled to a distal portion 115 (e.g., a cap). In some examples, the disclosed distal portion, e.g., cap, may be made integrally with distal end 104 of tube 102. The distal portion 115 may be temporarily or permanently attached to the tube's distal end 104. Temporary attachments may, for instance, be defined by a screw-fit, Luer taper, snap-fit, or compression fit arrangement. Furthermore, mechanisms for holding the attachment section to the ureteroscope, endoscope, catheter, etc. may be used, including, e.g., hose clamps, crimp bands, wrapped filaments, clips, etc. Permanent attachment may include welding, gluing, soldering, or other forms of attachment, or the desired cap may be integrally formed with tube 102. It will be appreciated that other forms of temporary or permanent attachment may be adopted without departing from the scope of the present disclosure. In some examples, the desired cap may be integral with a sheath which fits along a portion of the tube or a sheath that extends substantially the entire length of the endoscope.

In examples in which distal portion 115 is separate from tube 102, a proximal end of distal portion 115 may include a plurality of openings to align with distal openings of the lumens of tube 102. Depending on tube 102, the configuration of the plurality of openings may be adjusted. For example, a distal portion 115 designed to connect to tube 102 may include a first opening to align and fluidly connect with a first lumen 112 of FIG. 2. The first opening of the proximal end of distal portion 115 may match the first lumen 112 of FIG. 2, e.g., be substantially arc or curved in shape. Similarly, the proximal end of distal portion 115 may include a second and third opening to align and fluidly connect with second and third lumens 114 and 116, respectively. In examples in which tube 102 includes two semi-circular shaped lumens, the proximal end of distal portion 115 would similarly include two proximal openings in fluid communication with these lumens. A distal end of distal portion 115 may include any number, shape and/or configuration of distal openings. As shown in FIG. 3A, distal portion 115 may include a first distal opening and a second distal opening in fluid communication with first and second lumens 112 and 114, respectively. As shown, these distal openings are approximately semi-circular in shape and include angled walls. In addition, distal portion 115 includes a plurality of ports 122.

B. The Handle Portion

Handle portion 110 can be attached to tube 102 by, for example, welding, a locking configuration, adhesive, or integrally formed with tube 102. The handle portion 110 may include a plurality of ports. For example, a first port may place first lumen 112 of tube 102 in fluid communication with fluid supply assembly 140 and a second port may place second lumen 114 of tube 102 in fluid communication with vacuum source 150. Additional ports and lumens may be provided for supplying to distal end 104 of tube 102 a laser fiber coupled to laser control 130, an illumination device coupled to illumination source 160, and/or an imaging device coupled to the imaging apparatus 170. For example, first lumen 112 may include two ports, a first for connecting the fluid supply assembly 140 and a second for connecting laser fiber 120 and/or laser source 130. The handle portion 110 may include an actuating mechanism (not shown) to actuate one or more medical devices that may be located at the distal end 104 of tube 102. For example, the handle portion may include an actuating mechanism to power on or off the laser, the illumination device, and/or the imaging device.

The fluid supply assembly 140 may be any device and/or devices that can supply fluid (e.g., saline) to first lumen 112. The fluid supply assembly 140 may include, but is not limited to, a fluid source, a pump, a control system, a heat exchanger, a filter, a temperature sensor, a pressure sensor, a supply line, and/or various user input devices.

The vacuum source may be any device and/or devices that can provide suction to lumen 114 (e.g., house vacuum, vacuum pump, etc.). The vacuum source 150 may provide suction and allow the operator to vary the suction. The vacuum source 150 may be located near the patient or may be located remotely (such as a vacuum source located on a wall). In some examples, vacuum source 150 may be included in a single unit with fluid supply assembly 140. For example, fluid supply assembly 140 and vacuum source 150 may be the inlet and outlet, respectively, of a peristaltic pump.

C. Insertion and Operation of the Medical Device

Referring to FIG. 4, a patient's urinary tract includes urethra 402, bladder 404, ureter 406, and kidney 408. In some aspects of the present disclosure, the target area, e.g., the area in which particles, like kidney stones 470, are known or suspected to be located, may be within kidney 408. Referring to FIG. 4, an operator (e.g., a doctor or other medical professional) may insert distal end 105 of device 100 into the patient's urethra 402. The operator may advance distal portion 115 and tube 102 so that distal end 105 of distal portion 115 passes into and through the urinary bladder 404, into and through ureter 406, and into kidney 408. The operator may position a distal opening of first lumen 112 proximate a target area. A target area may be a site where stones (e.g., stone 470) are known or suspected to be located. An imaging device (e.g., imaging device 124 of FIG. 3A) may be utilized to determine the location of stone(s), as known in the art. The distal end 105 of distal portion 115 may be adjusted so that first lumen 112 and/or any medical instruments (e.g., laser fiber 120) disposed within first lumen 112 may be aimed at the located stone(s). Laser fiber 120 may then be introduced through first lumen 112 to distal end 104. Laser fiber 120 may be connected to and/or controlled by laser control 130.

As shown in FIG. 4, once the laser fiber is in a sufficient position to aim for a kidney stone (e.g., stone 470), the operator may initiate a laser control (e.g., laser control 130) to break up the kidney stone (e.g., stone 470).

The operator may connect first lumen 112 to fluid supply assembly 140 and/or may turn on previously connected fluid supply assembly 140 to introduce fluid through first lumen 112 to the target area. The fluid supply assembly 140 may then provide fluid, through first lumen 112, to the plurality of ports 122 and/or the distal end 105 of distal portion 115 and into kidney 408. In some examples, the fluid supplied is a saline solution, for example, 0.9% saline. Fluid supply assembly 140 and laser control 130 may be separately or simultaneously connected to first lumen 112. In addition, first lumen 112 may provide a pathway for other instruments (e.g., basket, grasper, etc.). In some examples, laser 120 and ports 122 may have separate lumens. For example, laser 120 may extend through first lumen 112 to distal end 105 of distal portion 115 and ports 122 may be in fluid communication with a separate lumen coupled with fluid supply assembly 140.

Before, after, or simultaneously with the operator turning on the fluid supply assembly 140 to introduce fluid through first lumen 112 to the target area, the operator may turn on the suction (e.g., vacuum source 150) to pull the stone fragments/dust (e.g., created by breaking stone 470) into second lumen 114. The arrows in FIG. 3A illustrate an exemplary path of irrigation fluid from first lumen 112 and ports 120 to second lumen 114.

In some examples, the fluid may be provided to first lumen 112 at a variety of flow rates. The fluid may be introduced in a continuous flow or pulsed. In some examples, the flow rate may be pulsed at a regular interval, e.g., every few seconds. The pulsed flow may be a flow that is either intermittently interrupted or simply reduced in rate on an intermittent basis. The flow rate may be pulsed at complex flow rate patterns such as periodic and aperiodic oscillatory patterns. A pulsed flow may be created in any way. In one example, the pulse flow may be created by a mechanical pump, e.g., a peristaltic pump. The mechanical pump may apply and release pressure on the fluid at intervals.

The flow rate of the introduced fluid may be balanced with the flow rate caused by the vacuum source. Balanced flow rates can be substantially equal, but need not be exactly equal. A balanced flow rate may be any flow rate that prevents harm to the patient. For example, a balanced flow rate may be any flow rate of the introduction of fluid in relationship to the flow rate of the suction that prevents hydronephrosis and/or prevents the kidney from collapsing due to no fluid in the system, as known in the art. The balanced flow rate may assist in maintaining a pressure equilibrium during operation of the device. In some examples, a pressure sensor may also be located at or near the target area and/or distal end 104 to assist in maintaining a pressure equilibrium.

In addition, the application of suction may improve the ability to break kidney stones by creating an anti-retropulsion effect. By applying suction through second lumen 114, a kidney stone may be pulled toward laser fiber 120, thus countering the effect of the laser energy pushing the kidney stone away. This configuration thus assists in generating the smaller stone fragments by pulling the stones into the reach of laser fiber 120. Further, by having at least some of the irrigation fluid provided from a side (e.g., ports 122 of distal portion 115) and suction from distal end 105 of distal portion 115, the inflow fluid is less likely to interfere with the vacuuming of the stone dust.

Once the operator determines kidney stone 470 has been broken into sufficiently small fragments (e.g., sufficiently small to pass naturally or to be suctioned into second lumen 114) or does not want to continue for other reasons, the laser process may be stopped. Once the stone fragments/dust have been sufficiently removed from the body through second lumen 114, the operator may cease introduction of irrigational fluid and/or stop suction. In some examples, the laser process, introduction of irrigational fluid, and/or application suction may all stop at the same time. In other examples, introduction of irrigational fluid and/or suction may continue after the laser process has stopped.

In some examples, fluid supply assembly 140 and/or vacuum source 150 do not operate at the same time as laser fiber 120. For example, the laser process may cease before introduction of fluid through first lumen 112 and/or application of suction through second lumen 114. In some examples, laser fiber 120 may be removed from first lumen 112 before fluid is introduced through first lumen 112.

At any point, an operator may additionally choose to move the device within the patient. For example, an operator may choose to move the distal end 105 of distal portion 115 to the site of an additional kidney stones and/or lower into the kidney or to a location in which additional stone fragments/dust have accumulated. The purpose of repositioning the distal end 105 may be to reach stones or stone fragments that need to be broken into smaller pieces and/or reach stone fragments/dust that the device was previously unable to suction out of the body and into second lumen 114. For example, some stone fragments/dust may be positioned proximally to the distal opening or positioned too distally to be captured by applied suction. An operator may reposition distal portion 115/tube 102 any number of times. Once repositioned, any or all of the previously described steps, e.g., the laser process, introduction of fluid, and/or application of suction, may be repeated at the new location.

Once an operator determines no more kidney stones can and/or should be broken apart and/or no more stone fragments/dust can and/or should be removed, the ureteroscope (e.g., tube 102) may be removed from the patient's body.

D. Laser Fiber Holder

FIGS. 5A-14 illustrate exemplary laser fiber holders for stabilizing a laser fiber. These laser fiber holders are designed to minimize movement of a laser fiber relative to the lumen or working channel it is disposed within. Stabilizing laser fibers relative to the lumen or working channel of a delivery device may also stabilize the laser fibers relative to an imaging device of the same delivery device. This may increase efficiency and lower the risk of misfiring, damaging healthy tissue as opposed to stones.

The laser fiber holders described herein are not limited to the delivery devices and/or lumens described herein. For example, laser fiber holder 180 of FIGS. 5A, 5B, and 6, laser fiber holder 780 of FIGS. 7A and 7B, laser fiber holder 880 of FIGS. 8A and 8B, laser fiber holder 980 of FIGS. 9A and 9B, laser fiber holder 1080 of FIGS. 10A and 10B, laser fiber holder 1180 of FIG. 11, laser fiber holders 1281 and 1283 of FIG. 12, laser fiber holder 1381 of FIG. 13, and/or laser fiber holder 1481 of FIG. 14 may be used in any device/lumen that may receive/deliver a laser e.g., a ureteroscope, an endoscope, catheter, etc. The laser fiber holder may be permanently or removably coupled to the delivery device and/or lumen it is disposed within. In some examples, like those shown above with respect to FIGS. 1-6, a laser fiber corresponding to a laser fiber holder may be disposed within a lumen that also supplies fluid. In other examples, the laser fiber may have a dedicated working channel that does not supply fluid. In some examples, the laser fiber may be disposed within the lumen applying suction.

The laser fiber holders may be formed of any suitable material having sufficient flexibility to traverse body cavities and tracts. In general, the laser fiber holders may be made of any suitable material that is compatible with living tissue or a living system. That is, laser fiber holders may be non-toxic or non-injurious, and it should not cause immunological reaction or rejection. In some examples, the laser fiber holders may be made of polymetric elastomers, rubber tubing, and/or medically approved polyvinylchloride tubing. Polymeric elastomers may be, for example, EVA (Ethylene vinyl acetate), silicone, polyurethane, and/or C-Flex.

FIGS. 5A and 5B illustrate an exemplary perspective view and an exemplary side view of an alternative distal end of the medical device of FIG. 1. Distal portion 115' may include any of the features or aspects of distal portion 115. Distal portion 115' may include substantially oval first lumen 112 and second lumen 114. Visualization device 126 may include a substantially rectangular imaging device surrounded by an illumination device (e.g., an LED). Distal portion 115' may include a laser fiber holder 180. Laser fiber holder 180 may be disposed within first lumen 112. In some examples, during insertion of distal portion 115' into the patient's body, laser fiber holder 180 may be entirely disposed within first lumen 112 in an inverted configuration. Once distal portion 115' is in position, laser fiber 120 may be inserted through first lumen 112 and pushing laser fiber 120 through opening 184 may transition laser fiber holder 180 from the inverted configuration to the extended configuration shown in FIGS. 5A, 5B, and 6.

Figure 6:
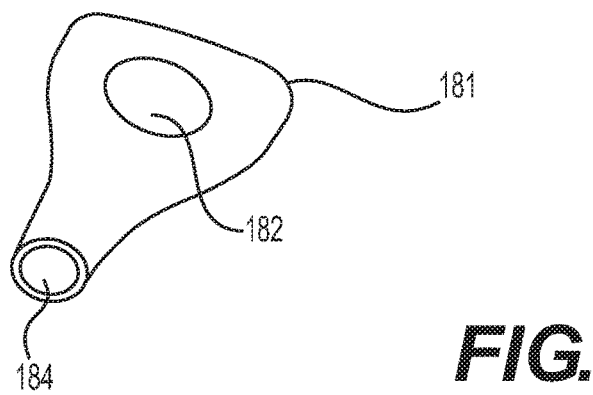
FIG. 6 illustrates an exemplary laser fiber holder.

FIG. 6 illustrates an exemplary laser fiber holder, for example, laser fiber holder 180 of FIGS. 5A and 5B. Laser fiber holder 180 may include four holes. A first proximal hole 181 to connect with the distal opening of first lumen 112. A second distal hole 184 or laser fiber 120 to extend through and into the patient's body. As shown in FIGS. 5A and 6, at least one hole 182 on a radial surface. As shown in FIG. 5A, irrigation fluid provided through lumen 112 may enter the patient's body through irrigation hole(s) 182. Laser fiber holder 180 may include any number of irrigation hole(s) 182, located on any radial surface. Laser fiber holder 180 may alternatively be used in lumens that apply suction. In these examples, hole(s) 182 may be used to apply suction.

FIGS. 7A and 7B illustrate an exemplary perspective view and exemplary cross-section of an alternative exemplary laser fiber holder 780. Laser fiber holder 780 is illustrated as hollow and substantially cylindrical, but may be any shape. Laser fiber holder 780 may include holder lumen 781 and/or a bi-direction ramp 752 affixed to a wall of holder lumen 781. Bi-directional ramp 752 may taper at its proximal and/or distal end. Ramp 752 may be used to direct a tool such as laser fiber 120 within any lumen and/or any delivery device (e.g., first lumen 112 of medical device 100). Ramp 752 may bias a laser fiber against one side of holder lumen 781, to stabilize the laser fiber and yet allow fluids to pass as shown in FIG. 7B. In some examples, ramp 752 may be manufactured by stamping. Stamping may create a side port from the wall of holder lumen that is manufactured to form ramp 752. Laser fiber holder 780 may be embedded into a lumen of a delivery device by the manufacturer or may be inserted into the lumen of the delivery device before the procedure. Laser fiber holder 780 may be secured within the lumen in any way known in the art, including, for example, friction fit. In some examples, laser fiber holder 780 may be inserted into the lumen of the delivery device entirely. In other examples, the laser fiber holder 780 may be inserted partially. For example, at least a portion of ramp 752 (and thus the side port created by the manufacturing of ramp 752) may be disposed distal of the lumen of the delivery device and thus, fluid within the lumen of the delivery device may flow through the created side port. In some examples, ramp 752 may be spring loaded such that it can collapse and recover its shape.

FIGS. 8A and 8B illustrate an exemplary perspective view and exemplary cross-section of an alternative exemplary laser fiber holder 880 with three bi-directional ramps 852, 854, and 856 and thus, three created side ports. Ramps 852, 854, and 856 may have any of the features of ramp 752 of FIGS. 7A and 7B. Similarly laser fiber holder 880 may have any of the features of laser fiber holder 780. Shown in FIG. 8B, a tool such as laser fiber 120 is centered in lumen 881 of laser fiber holder 880 and fluid can flow between the outer diameter of laser fiber 120 and the inner diameter of lumen 881 of laser fiber holder 880.

FIGS. 9A and 9B illustrate an exemplary perspective view and exemplary cross-section of an alternative exemplary laser fiber holder 980. Laser fiber holder 980 may be a stamping of a flat metal sheet and rolled into a U-shape. The U-shaped laser fiber holder 980 may be at least partially positioned within a lumen of a delivery device (e.g., first lumen 112 of medical device 100). The U-shape may be spring-loaded to anchor within the lumen of the delivery device. Bi-directional ramp 952, lumen 981, and/or laser fiber holder 980 of FIGS. 9A and 9B may have any of the features of ramp 752, lumen 781, and/or laser fiber holder 780 of FIGS. 7A and 7B, respectively.

FIGS. 10A and 10B illustrate an exemplary perspective view and exemplary cross-section of an alternative exemplary laser fiber holder 1080. Laser fiber holder 1080 may be a stamping of a flat metal sheet and rolled into a U-shape. The U-shaped laser fiber holder 1080 may be at least partially positioned within a lumen of a delivery device (e.g., first lumen 112 of medical device 100). The U-shape may be spring-loaded to anchor within the lumen of the delivery device. Bi-directional ramps 1052, 1054, and 1056, lumen 1081, and/or laser fiber holder 1080 of FIGS. 10A and 10B may have any of the features of ramps 852, 854, and 856, lumen 881, and/or laser fiber holder 880 of FIGS. 8A and 8B.

Figure 11:
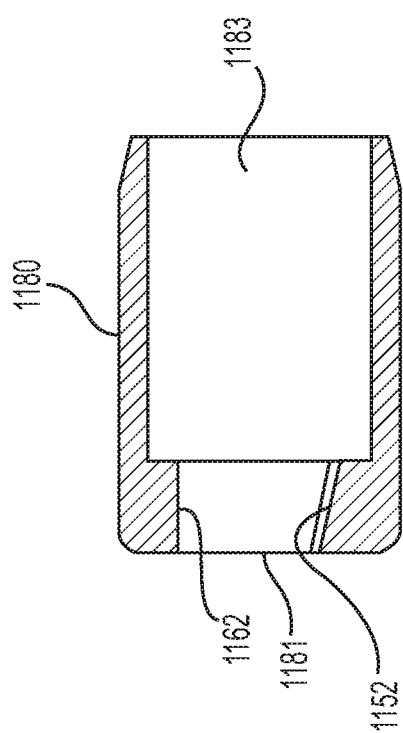
FIG. 11 illustrates an exemplary side view of an alternative exemplary laser fiber holder.

FIG. 11 illustrates an exemplary side view of an alternative exemplary laser fiber holder 1180. Laser fiber holder 1180 is a coupler that is used to removably attach and/or couple first lumen 1183 to a distal end of lumen of a delivery device. The distal end of lumen 1183 is coupled to ramp 1152. Ramp 1152 may bias a tool such as a laser fiber against wall 1186 of second lumen 1181. Ramp 1152 may stabilize the laser fiber and allow fluid to pass. Laser fiber holder 1180 may additionally or alternatively be used as a suction chamber to hold kidney stones with suction while the tool is used to fragment the stone. Laser fiber holder 1180 may be disposed of after a single patient use.

Figure 12:
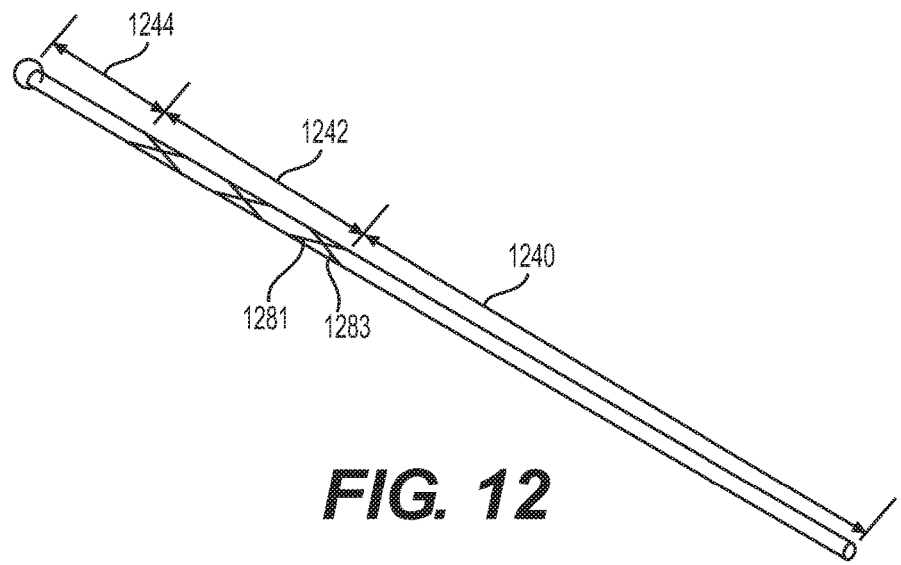
FIG. 12 illustrates an exemplary side view of an alternative exemplary laser fiber holder and a laser fiber.
Figure 13:
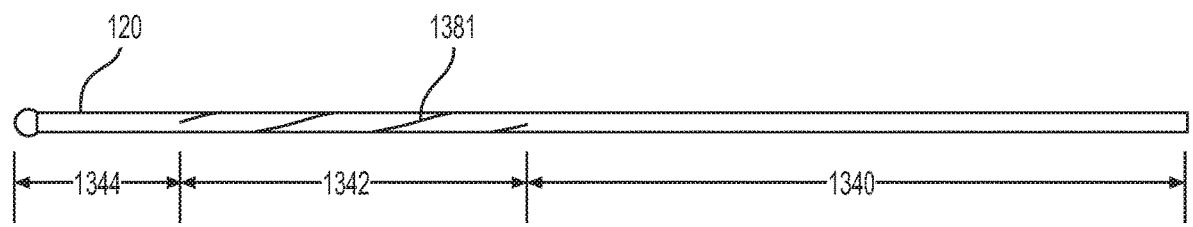
FIG. 13 illustrates an exemplary side view of an alternative exemplary laser fiber holder and a laser fiber.
Figure 14:
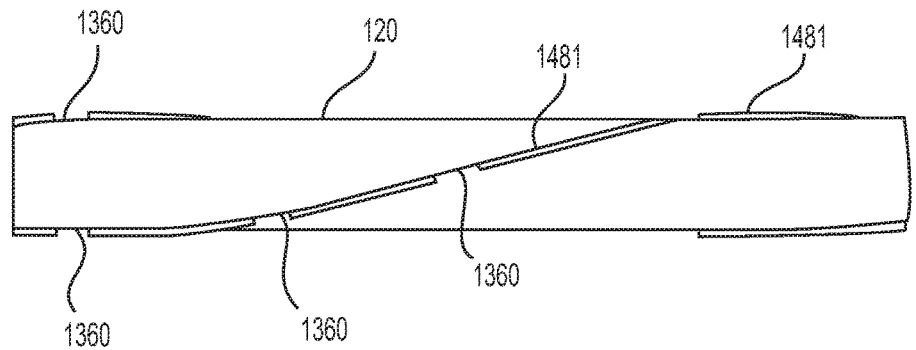
FIG. 14 illustrates an exemplary side view of an alternative exemplary laser fiber holder and a laser fiber.

FIG. 12-14 illustrate helix laser fiber holders. In some examples, these exemplary helixes may extend the entire length of the laser fiber 120. In other examples, the exemplary helixes may be offset from the tip, e.g., approximately 50 mm from the distal tip. Each helix may attach to the laser fiber or the interior surface of a lumen of a delivery device. The height of each helix in combination with the diameter of the laser fiber may be approximately the same as the inner diameter of the lumen of the delivery device. This may stabilize the laser fiber, and yet fluid may flow through the open spaces between pitches of each helix. Each of the below described helixes may be flexible enough to pass or be deflected within the lumen of the device.

FIG. 12 illustrates an exemplary side view of an alternative exemplary laser fiber holder 1281 wrapped around ball tip laser fiber 120. Laser fiber holder 1281 is a double helix coil. The helix 1281 protrudes from the surface of the laser fiber 120. The double helix is use to stabilize the laser fiber within a lumen of a delivery device and yet allow fluids to pass between each helix.

FIG. 13 illustrates an exemplary side view of an alternative exemplary laser fiber holder and a laser fiber. In this example, only one helix is used as laser fiber holder 1381. In some examples, a single helix laser fiber holder may have a tighter pitch than a double helix laser fiber holder.

FIG. 14 illustrates an exemplary side view of an alternative exemplary laser fiber holder 1481 and a laser fiber 120. The helical pattern may include intermittent gaps 1360 to assist with flow. At these gaps the height of the helix may be smaller than at other locations along the helix to allow fluid to pass through.

The many features of the disclosure are apparent from the detailed specification, and thus, it is intended by the appended claims to cover all such features of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other aspects of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
    a tube having a distal end, a proximal end, and an outer wall defining an outer circumference of the tube;
    a first lumen extending from the proximal end to the distal end of the tube and in fluid communication with the distal end and a plurality of side ports located within a plurality of recesses at a distal portion of the tube; and
    a second lumen extending from the proximal end to the distal end of the tube, wherein the second lumen includes only one opening at the distal end of the tube and is fluidly disconnected from each of the plurality of side ports,
    wherein a portion of the first lumen and a portion of the second lumen are each defined by the outer wall, and
    wherein the plurality of side ports are angled toward a distal end of the distal portion.

2. The medical device of claim 1, wherein the tube is in fluid communication with a cap located at the distal portion, and the cap is removably attached to the tube.

3. The medical device of claim 1, further comprising:
    a laser fiber disposed within the first lumen.

4. The medical device of claim 2, wherein the plurality of side ports are disposed on a circumference of the distal portion.

5. The medical device of claim 4, wherein the plurality of side ports are disposed on less than 270 degrees of the circumference of the distal portion.

6. The medical device of claim 1, further comprising:
    a vacuum source connected to the second lumen and a fluid supply assembly connected to the first lumen.

7. The medical device of claim 1, further comprising:
    an illumination device and an imaging device.

8. The medical device of claim 1, wherein the plurality of side ports include a plurality of linear rows.

9. The medical device of claim 1, wherein the plurality of side ports include at least three ports.

10. The medical device of claim 1, further comprising a third lumen extending between the first lumen and the second lumen, wherein the first lumen and the second lumen terminate proximally to a distalmost end of the third lumen.

11. The medical device of claim 1, wherein a diameter of a recess of the plurality of recesses is between approximately 1.5 times and approximately 3 times a diameter of a corresponding side port located within the recess.

12. A medical device, comprising:
a tube having a distal end and a proximal end and including a longitudinal axis;
a first lumen extending from the proximal end to the distal end of the tube, wherein the first lumen is in fluid communication with the distal end and a plurality of side ports located within a plurality of recesses at a distal portion of the tube, and wherein the first lumen is configured to be connected to a fluid supply to release fluid from the plurality of side ports; and
a second lumen extending from the proximal end to an opening at the distal end of the tube, wherein the second lumen is fluidly disconnected from each of the plurality of side ports, and wherein the second lumen is configured to be connected to a vacuum source to create a suction at the opening at the distal end of the second lumen,
wherein the plurality of side ports are angled toward a distal end of the distal portion causing the fluid to be released from the plurality of side ports at an angle that pushes particles toward the opening at the distal end of the second lumen for suctioning, and
wherein the distal end includes a pair of tapered edges so that, in a cross-section of the tube taken along a longitudinal axis of the tube, opposing sides of a radially exteriormost wall terminate proximally of a distalmost end of the tube such that an opening at a distalmost end of the first lumen and the opening at the distal end of the second lumen are both angled relative to the longitudinal axis of the tube.

13. The medical device of claim 12, wherein the first lumen is further configured to release the fluid from the fluid supply through the opening at the distalmost end of the first lumen, and wherein the second lumen is configured to receive material via a vacuum force from the created suction through only the opening at the distal end of the second lumen.

14. The medical device of claim 12, wherein the fluid is configured to be released from the plurality of side ports at an angle greater than approximately 10 degrees to the longitudinal axis of the tube and less than approximately 90 degrees to the longitudinal axis of the tube.

15. A medical device, comprising:
a tube having a distal end and a proximal end;
a distal portion located at the distal end of the tube;
a plurality of side ports located within a plurality of recesses at the distal portion;
a first lumen extending from the proximal end to the distal end of the tube, wherein the first lumen is in fluid communication with the plurality of side ports;
a second lumen extending from the proximal end to the distal end of the tube; and
a third lumen including an imaging device and an illumination device, wherein the third lumen is disposed between the first lumen and the second lumen, and wherein the imaging device is fixed such that a distalmost end of the imaging device is coplanar with a distalmost end of the third lumen.

16. The medical device of claim 15, wherein in a cross section of the tube, the cross section defined by a plane perpendicular to a longitudinal axis of the tube, the first lumen is arc-shaped, the second lumen is arc-shaped, and the third lumen is circular in shape.

17. The medical device of claim 16, wherein the first lumen includes a radially innermost wall defined by a circle having a first diameter, wherein a radially outermost wall defined by a circle having a second diameter, and wherein the first diameter and the second diameter are greater than a diameter of the third lumen.

18. The medical device of claim 15, wherein the first lumen is diametrically opposed to the second lumen about a central axis of the third lumen, and wherein the first lumen and the second lumen terminate proximally to a distalmost end of the third lumen.

19. The medical device of claim 15, wherein a fluid is configured to be supplied from a distalmost opening of the first lumen, wherein the medical device further comprises a medical instrument disposed in the first lumen, wherein the medical instrument is configured to extend toward a distal end of the medical device through the distalmost opening of the first lumen.

20. The medical device of claim 15, wherein the distal portion is integral to the distal end of the tube.

* * * * *